(12) United States Patent
Rahmlow et al.

(10) Patent No.: US 10,466,173 B2
(45) Date of Patent: Nov. 5, 2019

(54) OPTICAL FLOW CELL ASSEMBLY INCORPORATING A REPLACEABLE TRANSPARENT FLOW CELL

(71) Applicant: Wyatt Technology Corporation, Goleta, CA (US)

(72) Inventors: David Rahmlow, Goleta, CA (US); Matthew Greenstreet, Goleta, CA (US); Shiladitya Sen, Ventura, CA (US)

(73) Assignee: WYATT TECHNOLOGY CORPORATION, Goleta, CA (US)

( * ) Notice: Subject to any disclaimer, the term of this patent is extended or adjusted under 35 U.S.C. 154(b) by 0 days.

(21) Appl. No.: 15/727,398

(22) Filed: Oct. 6, 2017

(65) Prior Publication Data
US 2019/0107487 A1    Apr. 11, 2019

(51) Int. Cl.
| | |
|---|---|
| *G01N 21/53* | (2006.01) |
| *G01N 15/14* | (2006.01) |
| *G01N 21/39* | (2006.01) |
| *G01N 21/05* | (2006.01) |
| *G01N 30/74* | (2006.01) |
| *G01N 15/02* | (2006.01) |

(52) U.S. Cl.
CPC ....... *G01N 21/532* (2013.01); *G01N 15/0211* (2013.01); *G01N 15/1404* (2013.01); *G01N 15/1434* (2013.01); *G01N 21/05* (2013.01); *G01N 21/39* (2013.01); *G01N 30/74* (2013.01); *G01N 2015/1452* (2013.01); *G01N 2021/058* (2013.01); *G01N 2030/746* (2013.01)

(58) Field of Classification Search
CPC .. G01N 21/532; G01N 30/74; G01N 15/1434; G01N 21/05; G01N 21/39; G01N 15/1404; G01N 2030/746; G01N 2021/058; G01N 2015/1452; G01N 21/01; G01N 21/51
See application file for complete search history.

(56) References Cited

U.S. PATENT DOCUMENTS

| | | | | |
|---|---|---|---|---|
| 3,512,163 | A | * | 5/1970 | Pelavin .................. G01N 21/05 250/573 |
| 4,616,927 | A | * | 10/1986 | Phillips .................. G01N 21/03 356/338 |
| 4,907,884 | A | * | 3/1990 | Philips .................. G01N 21/03 356/336 |

(Continued)

OTHER PUBLICATIONS

Wyatt Technology Corporation, Dawn Heleos II promotional literature, 2007, Santa Barbara, US.

*Primary Examiner* — Mohamed K Amara
(74) *Attorney, Agent, or Firm* — Leonard T. Guzman

(57) ABSTRACT

A new liquid flow cell assembly for light scattering measurements is disclosed which utilized a floating manifold system. The assembly operates with minimal stacked tolerances by aligning the cell to the windows within a manifold and independently aligning the cell to the read head directly. This configuration enables the ability to replace the flow cell or the flow cell/manifold assembly within a light scattering instrument without the need to realign the flow through elements with the light scattering illumination source while still maintaining reproducible, quality data. Some embodiments employ wide bore cells which enable the measurement of process analytic technology (PAT) including online monitoring of reactions.

18 Claims, 13 Drawing Sheets

(56) References Cited

U.S. PATENT DOCUMENTS

| | | | | |
|---|---|---|---|---|
| 5,030,002 A * | 7/1991 | North, Jr. | G01N 15/1404 | 209/3.1 |
| 5,168,326 A * | 12/1992 | Tokieda | G01J 4/04 | 356/244 |
| 5,220,401 A * | 6/1993 | Milosevic | G01N 21/552 | 356/244 |
| 5,305,071 A * | 4/1994 | Wyatt | G01N 21/4133 | 356/128 |
| 5,404,217 A * | 4/1995 | Janik | G01N 15/1404 | 250/576 |
| 5,691,486 A * | 11/1997 | Behringer | G01N 15/1404 | 422/540 |
| 5,844,685 A * | 12/1998 | Gontin | G01N 15/1436 | 356/433 |
| 5,953,681 A * | 9/1999 | Cantatore | G01N 15/14 | 702/31 |
| 6,042,249 A * | 3/2000 | Spangenberg | G01N 15/14 | 362/259 |
| 6,426,794 B1 * | 7/2002 | Trainoff | G01N 21/05 | 356/246 |
| 6,452,672 B1 | 9/2002 | Trainoff | | |
| 6,643,018 B2 * | 11/2003 | Chavanne | G01N 21/05 | 356/337 |
| 7,630,076 B2 * | 12/2009 | Kalonia | G01N 21/05 | 356/338 |
| 7,982,875 B2 | 7/2011 | Trainoff | | |
| 9,001,319 B2 * | 4/2015 | Tokhtuev | G01N 21/15 | 356/246 |
| 9,146,192 B2 * | 9/2015 | Some | G01N 21/47 | |
| 2003/0209647 A1 * | 11/2003 | Miller | G01N 21/05 | 248/694 |
| 2006/0200070 A1 * | 9/2006 | Callicoat | A61B 5/14532 | 604/66 |
| 2010/0315637 A1 * | 12/2010 | Trainoff | G01N 21/51 | 356/337 |
| 2012/0059234 A1 * | 3/2012 | Barrett | A61B 5/14557 | 600/326 |
| 2016/0091426 A1 * | 3/2016 | DiCesare | G01N 21/05 | 250/435 |
| 2017/0248621 A1 * | 8/2017 | Putnam | G01N 35/00029 | |
| 2017/0268981 A1 * | 9/2017 | Diebold | G01N 15/1434 | |
| 2017/0370826 A1 * | 12/2017 | Coombs | G01N 21/05 | |
| 2018/0117587 A1 * | 5/2018 | Lemoine | B01L 3/502715 | |
| 2019/0107487 A1 * | 4/2019 | Rahmlow | G01N 21/532 | |

\* cited by examiner

Side view

Top view

Top view

Side view

Front view

Side view

Top view

Side view

Top view
(Cell/manifold)

Side view

Bottom view
(cell only)

Horizontal sweep

Horizontal sweep

Vertical sweep

Vertical sweep

OPTICAL FLOW CELL ASSEMBLY INCORPORATING A REPLACEABLE TRANSPARENT FLOW CELL

RELATED APPLICATIONS AND PATENTS

The following patents relate to the measurement of light scattering from a liquid sample contained in an optical flow-through cell and are hereby incorporated by reference:
U.S. Pat. No. 4,616,927, S. D. Phillips, J. M. Reece, and P. J. Wyatt, "Sample cell for light scattering measurements," issued Oct. 14, 1986.
U.S. Pat. No. 4,907,884, P. J. Wyatt and S. D. Phillips, "Sample cell monitoring system," issued Mar. 13, 1990.
U.S. Pat. No. 5,404,217, G. R. Janik and J. F. Magolske, "Laser liquid flow cell manifold system and method for assembly," issued Apr. 4, 1995.
U.S. Pat. No. 6,452,672 B1, S. P. Trainoff, "Self cleaning optical flow cell," issued Sep. 17, 2002.
U.S. Pat. No. 7,982,875 B2, S. P. Trainoff, "Method and apparatus for measuring the scattered light signals from a liquid sample," issued Jul. 19, 2011.

BACKGROUND

Throughout this specification, the term "particle" refers to the constituents of liquid sample aliquots that may be molecules of varying types and sizes, nanoparticles, virus like particles, liposomes, emulsions, bacteria, colloids, etc. Their size range may lie between 1 nm and several thousand micrometers.

Solutions containing solutes such as molecules, viruses, nanoparticles, liposomes, etc. are often analyzed after their constituent fractions are separated by liquid chromatography technique such as size exclusion chromatography (SEC), which is also referred to as high performance liquid chromatography (HPLC) or another separation technique such as field flow fractionation (FFF), hydrophobic interaction chromatography (HIC), or ion exchange chromatography (IEX). Such measurements may include determination of solute concentration, solution viscosity, and light scattering properties. The latter measurement used in combination with a corresponding concentration determination may be used to derive the size, molar mass, aggregation, and associations of the solutions constituent elements. To improve these measurements the light scattering detection is frequently performed by measuring the light scattered by the separated sample at a plurality of angles with respect to the direction illuminating light beam. This technique of measuring the intensity of the light scattered by a liquid sample as a function of angle is referred to as multiangle light scattering (MALS).

MALS measurements may also be performed in a "batch mode" wherein an unfractionated, prepared liquid sample contained within a scintillation vial or cuvette is placed into the path of the illuminating beam. An alternative to the traditional batch measurement wherein the sample is injected, unfractionated into a flow cell is generally referred to as "stop-flow" or "microbatch" mode. In microbatch mode, after a measurement is made, the sample is removed from the flow cell by an injection of another sample or solvent through the flow cell inlet. The present invention is equally relevant to both microbatch and the standard flow-through measurements discussed above.

While flow through MALS cells have taken many forms through the years, the ease and reliability of MALS measurements took a dramatic step forward with the introduction of an axial flow cell described by Phillips, et. al. in U.S. Pat. No. 4,616,927 (issued Oct. 14, 1986). The basic structure of the axial cell assembly as described by Phillips is shown in FIG. 1. A right circular glass cylinder 101 contains a small polished bore 102 drilled through a diameter about midway between the cylinder's base and top. Flow through fixtures 103 and 108 contain a channel 104 through which a liquid sample may pass. These fixtures also house optical windows 105 which are held into the fixtures by retaining elements 106. A seal is maintained between the window 105 and the channel 104 by a gasket or o-ring. Fluid passes from the inlet fixture 103 through a connection tube 107 that directs the sample to flow through the cylindrical flow cell 101 and then through the exit fixture 108. From there the sample may flow to waste or another detector or a sample reclamation system. A light beam 109, generally from a laser source, is directed to pass through the optical windows, 105 along the same path as the liquid sample. This entire assembly 100 was then placed into a read head with spaces milled therein rigidly hold the elements in place as well as possible. In general, a plurality of photodetectors (not shown) are also rigidly held within the read head positioned circumferentially about the center of the flow cell. These photodetectors gather light scattered from the light beam by the sample as it passes through the bore 102. Once the flow cell assembly was fitted into the read head, the laser was aligned such that the beam 109 passes through the center of the bore 102 without grazing its walls.

A problem associated with all flow through optical cells, and in particular those which measure static light scattering, is the inevitable presence of contaminants accumulating within the cell itself. These contaminants can be introduced from various sources, including detritus shed upstream detectors or preparative systems, such as chromatography columns, or they can be accidentally introduced by direct injection in mircobatch measurements. Even the samples themselves may contribute to dirtying the cell by forming aggregates with a strong affinity for the internal optical systems. Once a cell is contaminated, it must be cleaned, either in situ by flushing or more aggressive means such as sonication, as described by Trainoff in U.S. Pat. No. 6,452,672 B1 (Issued Sep. 17, 2002), or by removing the cell glass itself and performing a manual cleaning. While in situ cleaning techniques can be effective in the short term, most MALS cells must be removed and cleaned manually on a somewhat regular basis. Flow cell cleaning usually requires some expertise and extreme caution to be certain none of the inner or outer surfaces are soiled by contaminants such as fingerprints, residues and particulates. Further, damage to the cell can occur both during manual cleaning, and albeit less frequently, during normal instrument operation. It is therefore inevitable that the flow cell will need to be removed from the assembly from time to time.

One limitation of the Phillips cell is the difficulty associated with realignment of its optical elements after disassembly for cleaning or other maintenance. In the Phillips system, the optical axis is defined according to the position of at least three elements, the inlet and outlet fixtures 103 and 108, each of which house windows through which the beam will pass, and the bore 102 of the flow cell 101 itself. If any of these items are in misalignment, the optical system may fail. What is more, the position of the connection elements 107 at least partly define the height of the bore relative to the windows, so any wear or issues associated with orientation of the cylindrical connection elements may cause the entire bore to be canted. For these reasons every time the cell is removed from the instrument, every optical element in the chain must be realigned to ensure the beam is reliably able to pass through both windows and the bore of the flow cell without grazing any interfaces. Further, the lack of any orienting or registration elements on the glass cell itself contributed to the possibility of misalignment due to placing the cell in 180° from its originally aligned position, as well the possibility of play in the connection elements allowing the bore to be positioned non-parallel to the optical axis defined by the position of the windows. These limitations made realignment of the Phillips cell cumbersome every time the cell was removed from the system.

These problems relating to effectively reproducing the alignment conditions of the cell relative to the beam when the cell was removed were addressed by Janik, et. al, in U.S. Pat. No. 5,404,217 (Issued Apr. 4, 1995), hereinafter referred to as the '217 patent. Janik describes a rigidly connected flow cell manifold housing all elements that may then be removed as a single unit from the optical bench of the MALS instrument. As shown in FIG. 2, the flow cell 201 not contains two flattened surfaces 202 at the inlet and outlet of the bore. These surfaces serve to register the cell and prevent any rotation thereof relative to the inlet and outlet manifold halves 203 and 204. One embodiment of the Janik invention includes a step 205 milled into the glass cell 201 itself. This step is pressed up against either pins or a seat present in the manifold halves, further ensuring consistent directional alignment of the bore with the manifold halves. Each manifold half in turn contains an inlet or outlet 206 milled into the top surface. Fluiding bearing tubing is connected to these ports by means of an appropriate fitting. One of these ports 206 directs the sample via a fluid channel to the bore 207, parallel thereto, of the flow cell 201. The flow cell is sandwiched between the manifold halves and sealed thereto by gaskets or o-rings. Fluid leaving the other end of the bore is directed to the outlet port 206 and exists the instrument to proceed to waste, another analysis instrument or a sample recover system. Each manifold half also contains an optical window that allows a laser beam to pass along the fluid path in the manifold halves and through the flow cell bore. As in the Phillips invention, Janik directs a laser beam through the window within the inlet manifold half 203, and emerging from the window in the outlet manifold half 204 after passing through the bore of the flow cell without grazing any surfaces contained therein. The manifold halves are held together by bolts, and are rigidly connected to a base plate 208. Once fully assembled, the flow cell manifold system is placed within the read head of a MALS instrument to which the assembly had previously been aligned. This method facilitates the reassembly of the instrument after flow cell cleaning and provides reliable reproducibility of alignment for a particular manifold assembly with a particular flow cell and its associated MALS instrument. Thus Janik enabled a user to disassemble and reassemble the flow cell system without the need to realign the laser after each cleaning.

In all cases discussed thus far, it should be noted that each element of the optical system, in particular the flow cell itself, was mated with the other elements for the life of the alignment. Thus, in all cases, before the present invention it was not possible to replace a flow cell with a different cell without the need to realign the system. Of course the realignment of an optical system adds further complexity to the entire process and is generally performed only by well trained personnel, generally requiring the shipment of the entire system back to the manufacturer. It is an objective of the present invention to enable the replacement of one optical flow cell with another within the same MALS instrument without the need to optically realign the system. It is a further objective of the invention to enable the end user to reliably replace the flow cell without specialized equipment or knowhow. It is another objective of the invention to facilitate the use of distinct flow cells with specific properties, such as refractive index differences or varying bore widths within a MALS instrument. Another objective of the invention is to enable Process Analytic Technology (PAT) to monitor reactions by utilizing bore widths compatible with this technology and permitting the replacement of flow cells online without the need to halt the reaction system.

BRIEF DESCRIPTION OF THE SEVERAL VIEWS OF THE DRAWINGS

FIG. 3 illustrates the requirements of degrees of constraint in relation to two flow cell orientations.

A DETAILED DESCRIPTION OF THE INVENTION

Figure 1:
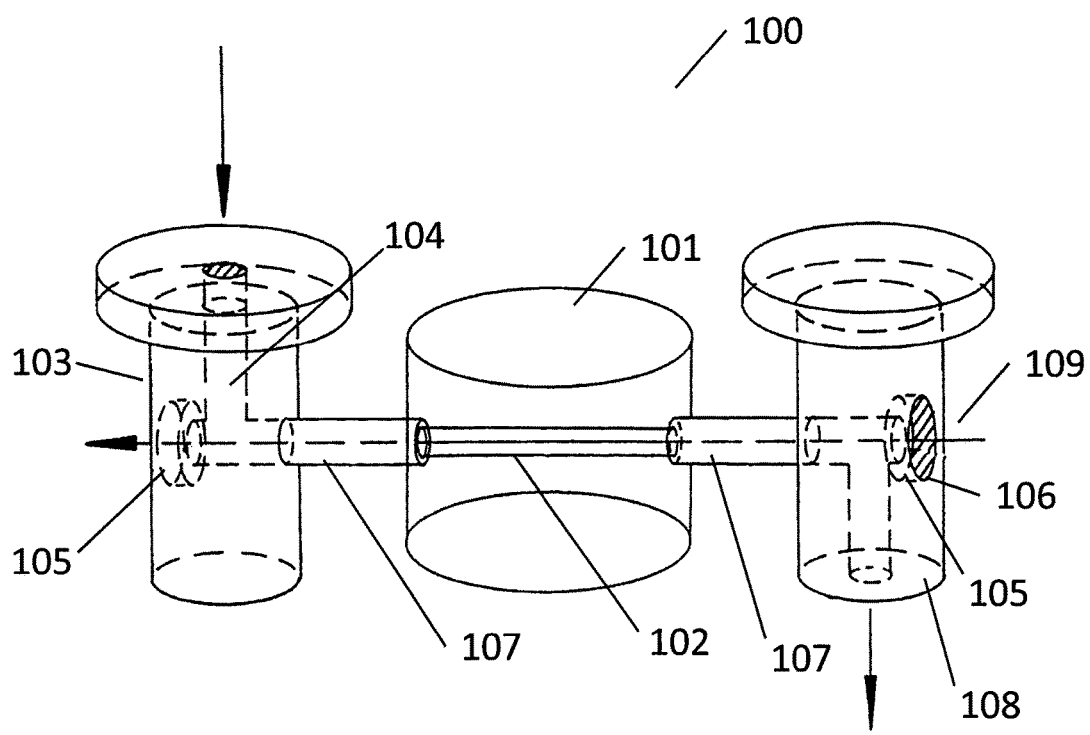
FIG. 1 shows a flow cell assembly according to Phillips including fittings for insertion into a light scattering photometer.
Figure 2:
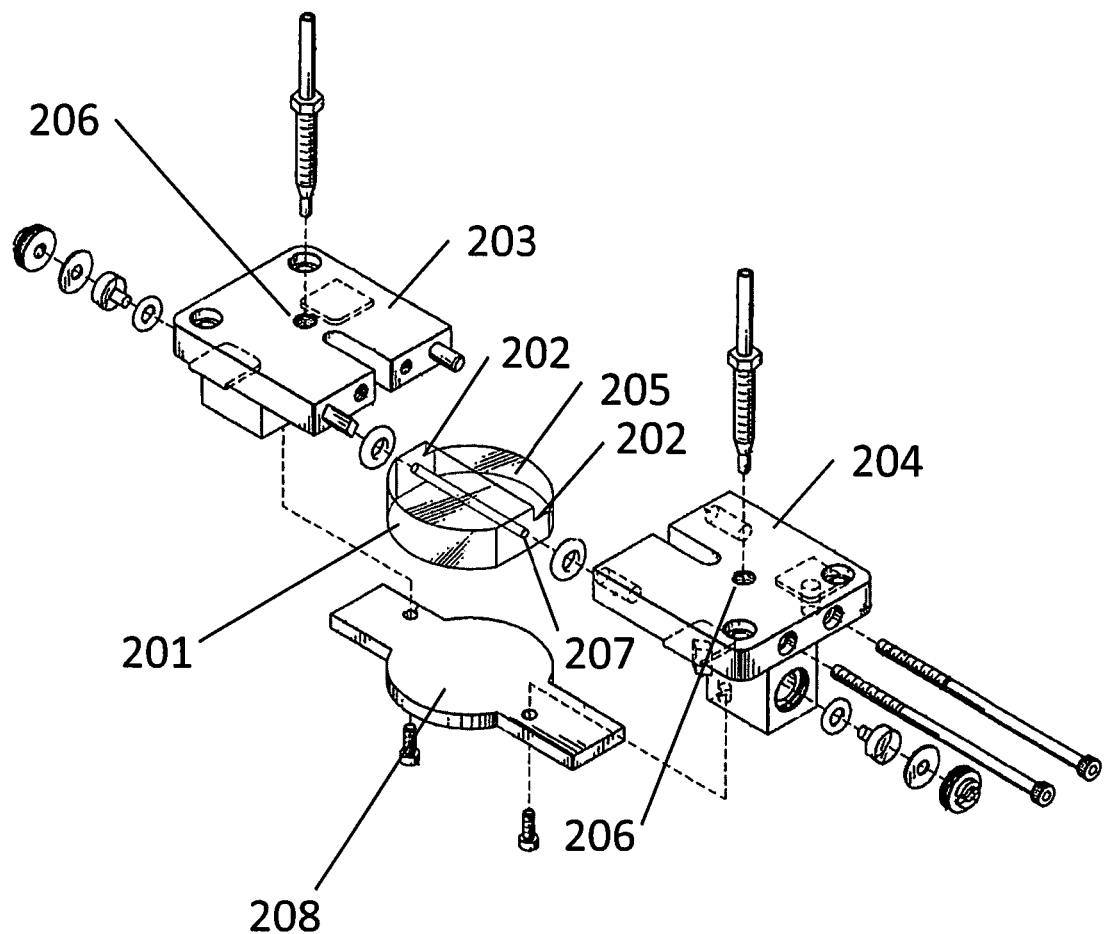
FIG. 2 shows elements of the improved manifold and flow cell according to Janik.

There are many instances in which the flow cell of a MALS or other light scattering instrument may need to be removed from the instrument in which it is housed. In addition to routine maintenance and cleaning, it is sometimes necessary to change the index of refraction of the cell by replacing it in order to index match the sample solvent with that of the flow cell to improve the signals received at a plurality of angles. Further, while flow cells are generally constructed from some form of glass, transparent polymers may also serve, under certain conditions, as the flow cell material, and some solvents are simply incompatible with certain flow cell materials. Therefore in order improve the versatility of a single light scattering instrument it is beneficial to enable the end user to replace the flow cell with another under these conditions. Further, as discussed previously, cleaning the flow cell itself can be a meticulous and laborious job requiring significant skill, care and time, and under many laboratory conditions, the light scattering instrument is in almost constant use, and therefore downtime associated with flow cell cleaning can significantly disrupt the laboratory workflow. This is particularly relevant for PAT applications, wherein the system is flowing constantly as the monitoring of reactions is performed in real-time, and any significant downtime due to a malfunctioning flow cell can not only disrupt laboratory experiments, but also the very process which is being monitored, and might cause critical stop-reaction triggers to be missed. Real time monitoring of polymer reactions is discussed in depth by J. Y. Gui, et. al., in U.S. Pat. No. 6,635,224 B1 (Issued Oct. 21, 2003), incorporated herein by reference, and many of the methods discussed therein are also relevant to monitoring of protein reactions. It is therefore clearly desirous to enable a means whereby light scattering flow cell can be removed from a light scattering system without the excessive downtime required to realign the systems optical elements. It is an objective of this invention to provide means to enable a simple "drop in" replacement cell to be used in light scattering instruments.

As discussed above, the necessity to realign the optical elements in a light scattering system was somewhat mitigated by Janik's '217 patent, by mating a flow cell to a manifold, and providing means including pins, pads and keyed surfaces, retaining, thereby, proper alignment after the cell is removed, cleaned and replaced in the instrument read head, as it was the complete manifold assembly, not the flow cell itself, that was initially aligned with instrument optics. Unfortunately, however, each element of the Janik assembly had its own tolerances, and thus it was not generally possible to replace a manifold assembly with a second manifold assembly and reliably retain optical alignment, as the '217 invention stacks at least four levels of tolerances:

1. The flow cell to the top manifold;
2. The assembled top manifold's bottom surface bosses to the read head;
3. The read head to the laser source; and
4. The tolerances of the flow cell itself, including the position of the bore with respect to the glass alignment surfaces.

Because in the Janik implementation the cell glass was aligned to the manifold assembly, and then the manifold assembly aligned to the read head, deviations in exact measurements in each level of the mechanical interfaces, though each element is within its required tolerance, could easily result in an instrument where the originally aligned cell and its associated assembly performs flawlessly, but a secondary manifold assembly inserted into the read head resulting in the beam grazing the inner bore, and producing poor light scattering measurements. It is an objective of the present invention to improve the interchangeability of cells and cell assemblies by reducing the stacking of tolerances.

In order to overcome the limitations of conventional light scattering cell assemblies, the present invention utilizes a "floating manifold" while maintaining tight controls on measurement specifications of the flow cell itself. In preferred embodiments, the method of "exact-constraint design" (sometimes called "kinematic design," and these terms may be used interchangeably in this specification) is employed to clearly define registration between the measurement cell and the read head. In our application, exact-constraint design maximizes the efficiency of the restriction the translational and rotational degrees of freedom of the cell within the read head, and in many embodiments is also employed to restrict the range of motion of optical elements contained within a floating manifold, including the flow cell. As chromatographic analysis proceeds to ever smaller sample sizes and their associated narrow peaks, it is more important than ever to maintain a very small sample volume required for measurement in any analytical instrument, requiring thereby, for most modern applications, a very small sample channel cross section. In order to meet these strict tolerance requirements, the present invention minimizes the interfaces over prior art systems while retaining or improving flexibility, robustness, and simplicity the servicing of a light scattering detection system. In particular, many embodiments of the present invention employ a floating manifold to reduce the stacking of tolerances and permitting the flow cell to be independently aligned to both a widow holding manifold and the laser containing read head independently. The floating manifold assembly and its associated tolerances are thereby effectively removed from the alignment between the beam and the measurement volume within the sample channel. Exact-constraint design can be further employed to generalize the invention to many embodiments, configurations and geometries.

In all cases, the present invention relates to improving light scattering detection through the illumination of a sample, generally contained as a liquid suspension, that is contained within a measurement volume. In order to achieve this end, a light beam, generally a laser, must pass through the measurement volume, and one or more detectors must be able to detect light scattered from the illuminating beam by the sample, and therefore, a primary objective of this invention is to enable the simplification of the process of aligning optical elements and minimizing the number of critical alignment elements, while defining the maximum allowable tolerance for critical alignment elements. In most embodiments, including those presented below, the measurement volume is a flow through channel, generally a bore with a circular cross section. It should be noted, however, that the channel need not be circular in cross section, but rather, could be of any shape wherein light scattered from the sample can be detected, and while the term "bore" is used throughout much of the specification to indicate the path in which this measurement volume is contained, in most embodiments and geometries, the bore could still take another form, such as a channel with a square, rectangular, triangular, etc., cross section and still be but one embodiment of the present invention. In embodiments where the flow path is co-linear with the beam, transparent windows are a part of the overall system, whether they are a part of the measurement cell itself, or, as is generally the case, are additional elements held in place by a manifold element such as that used by Janik. Windows may not be necessary in embodiments where the flow is not co-linear with the beam direction. The primary benefit of the present invention is to provide a system whereby a beam contained within a read head can reliably be expected to illuminate a sample volume within a sample cell and enabling light scattered from the sample volume to be collected by a detector or detectors also located within the read head, and wherein appropriately manufactured sample cell can be swapped into any appropriate read head without additional, cumbersome alignment steps. According to this invention, this objective is accomplished by registering the flow cell directly to read head while minimizing extraneous contact points and/or utilizing exact constraint design.

Figure 3A:
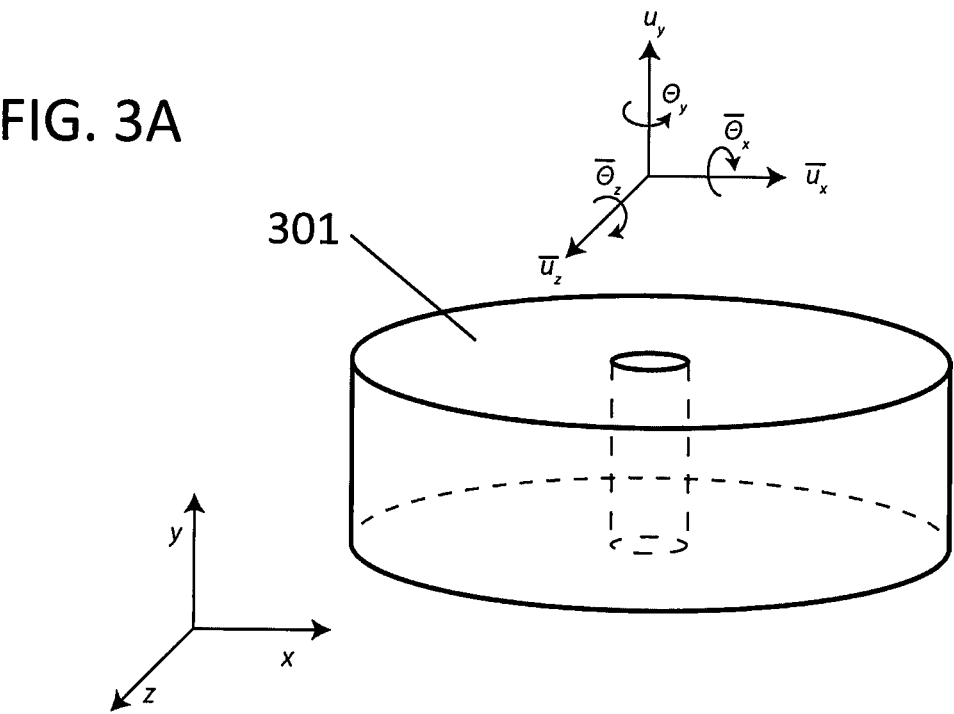
FIG. 3A shows a sample cell with a channel along the cylindrical axis of the cell.
Figure 3B:
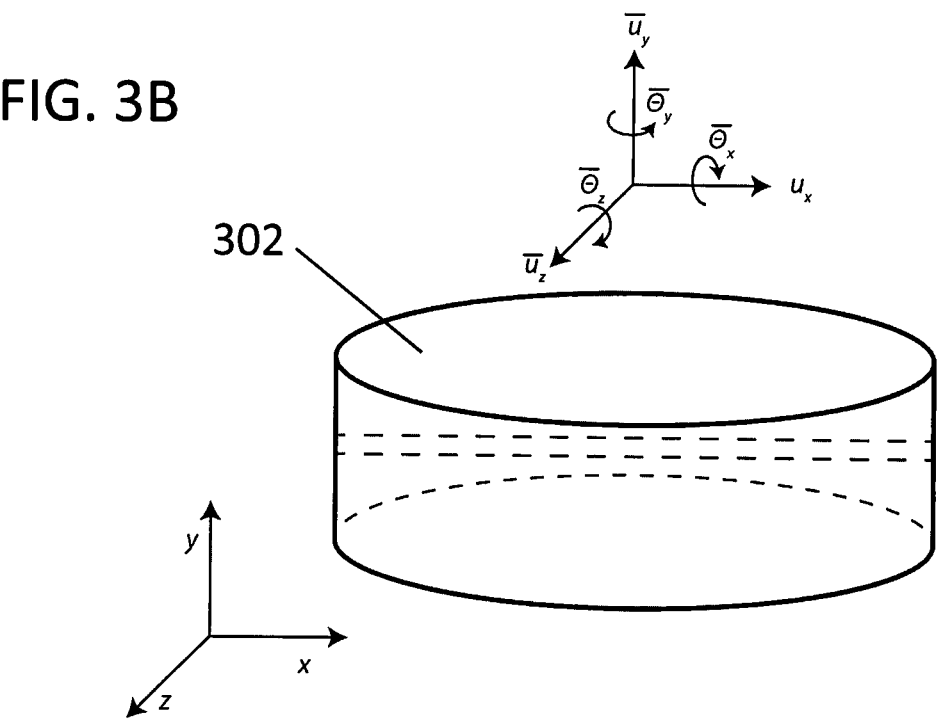
FIG. 3B shows a sample cell wherein the flow path and the laser path are collinear.

For purposes of illustration and to explore the primary cell orientations many preferred embodiments of the invention, FIG. 3 shows the constraints needed for two possible flow cell orientations. In both cases, the flow cells shown 301 and 302 are cylindrical in shape. The reference axis shown in each example and defined as ground, is attached to the read head. $u_x$ symbols denote translational displacement along the x axis. $\theta_x$ symbols denote rotational displacement along the y axis. The presence of a bar over the displacement symbols denotes that this particular displacement is a degree of constraint, that is, embodiments of the invention with this vertical flow cell orientation require these displacements to be constrained, while the absence of a bar over the displacement symbols denotes that the displacement is a degree of freedom. In the first example shown in FIG. 3A, the cell 301 has what is commonly referred to as a vertical sample channel, that is, the sample channel is a bore drilled along the cylindrical axis of the cell, in this case the y axis is parallel to the bore. This vertical flow cell, wherein the laser crosses perpendicularly to the flow path, requires four degrees of constraint, that is, translationally the cell must be constrained in the x and z axes, and rotationally about the $\theta_x$ and $\theta_z$ axes, however, exact constraint is not required along the y axis or rotationally about the $\theta_y$ axis. Therefore, in order for the flow cell to be kinematically registered to the read head in which the laser is mounted, a minimum of four degrees of constraint are required. FIG. 3B shows what is generally called a horizontal (or parallel), cylindrical flow cell, that is one wherein the flow path and the laser path are collinear, and where the x axis is parallel to the flow cell channel. For this embodiment to be kinmatically registered to the read head, a minimum of five degrees of constraint are required, that is, translational restraint along the y and z axes and rotational constraint in all three θ axes. In order to provide the necessary degrees of constraint, at least as many distinct contact points or surfaces as the number of degrees of freedom desired to constrain are required. For example on the vertical flow cell shown in FIG. 3A would need at least four contact point of surfaces, thought one may overconstrain with 5 or 6 contact points if so desired. It should also be noted that there are many engineering choices which can be made to simplify the number of contact points needed, for example straight line contact is equivalent to two point contacts. One may choose several ways to implement these contacts via an alignment posts, v-grooves, cones, etc., and some such example embodiments of the invention utilizing several methods of exact constraint design are discussed below, all of which are only specific implementations of the invention.

Figure 4:
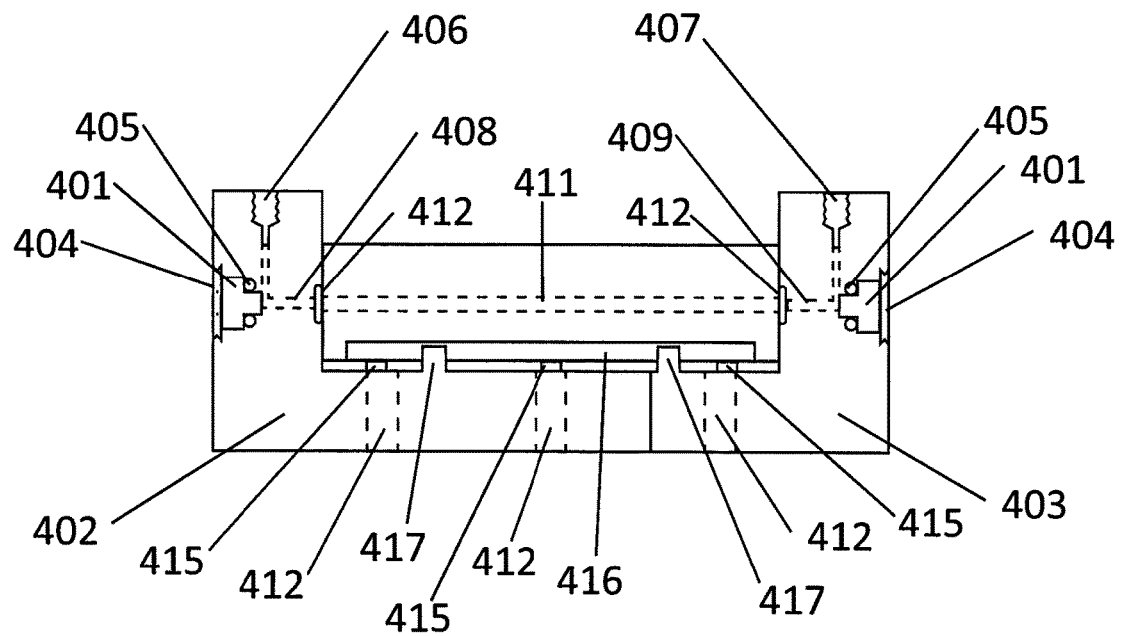
FIG. 4 shows a side view and a top view of an embodiment of the floating manifold of the present invention wherein stacked tolerances are reduced.
Figure 4:
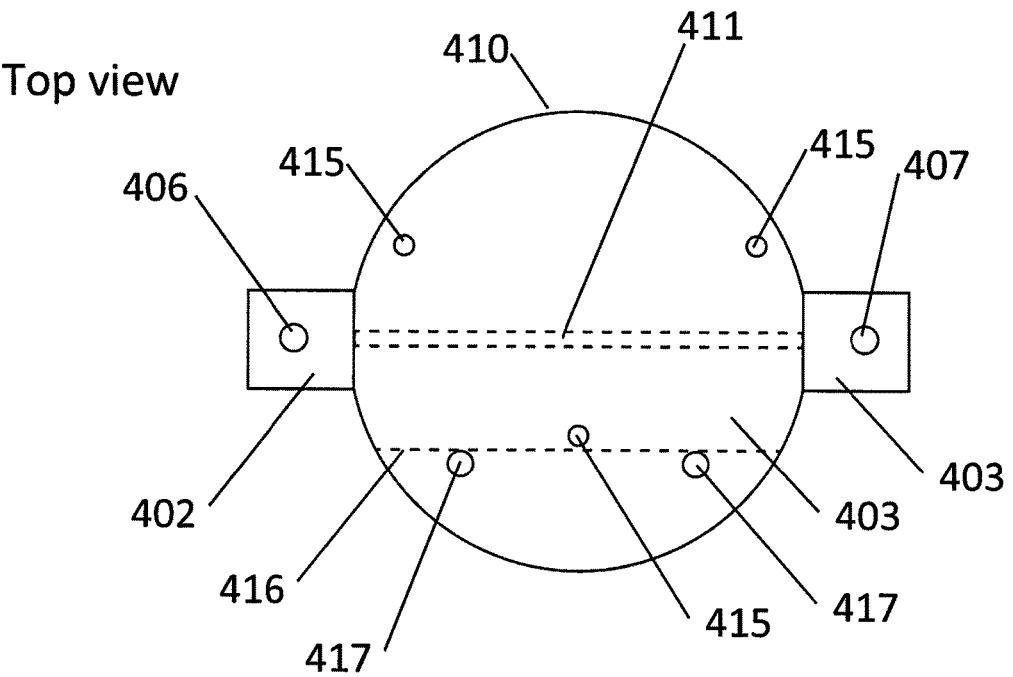

One embodiment of the manifold element utilized in some embodiments of the present invention, which is a variation of a traditional flow cell configuration is shown in FIG. 4. In a similar manner to the Janik design, the optical windows 401 are housed within each section of a manifold element 402 and 403, held into place by retaining washers 404, and sealed by o-rings or gaskets 405. The retaining washers 404 are generally threaded to match receiving threaded ports with the manifold sections. A sample inlet port 406 permits the injection of liquid sample into the manifold, and directs the sample to the optical window 401. The fluid is then directed through a fluid inlet path 408. The flow cell 410 is sandwiched between the two manifold sections 402 and 403 and the ends of the cell bore 411 are sealed between the fluid inlet and outlet paths (408 and 409 respectively) by o-rings or gaskets 412. The x-y plane is defined by three precision milled posts 415 upon which the bottom planar surface of the cell is placed. The posts may have a flat top surface in contact with the bottom surface of the cell, or they may be hemispherical, in which case apex of each hemisphere makes contact with the planar surface at only one point, and thus exactly defining the plane upon which the cell rests within the manifold. An incorporated step 416 within the flow cell 410 is placed in contact with two alignment pins 417, generally precision milled cylinders. The plane defined by the step 416 when registered against the single vertical line of contact of each post 417 defines the cell location in the horizontal direction, permitting thereby alignment of the bore 411 with the fluid pathways 408 and 409 and the optical windows 404. The two manifold sections 402 and 403 are held together by bolts 414 placed through one manifold section and into an engaging threaded hole in the other manifold section. In contrast to the Janik assembly, the manifold sections are connected beneath the flow cell rather than above it. Another critical element of the present inventive flow cell assembly are the three vertical holes 412 machined into the bottom surface of the manifold, which allow aligning elements of the read head direct access to the bottom surface of the cell as discussed below. In accordance with exact-constraint design, the three alignment posts in contact with the planar bottom surface of the cell and the two alignment pins in contact with the step define the relative position of all elements of the manifold to all elements of the flow cell.

The fully assembled manifold structure can then be placed in an alignment fixture to verify that the optical windows 401 and bore 411 are properly aligned, such that the laser beam passes through the windows and bore without intersecting any surfaces that might cause improper light scattering measurements. Once this alignment is verified, the cell assembly may be inserted into the read head.

Figure 5:
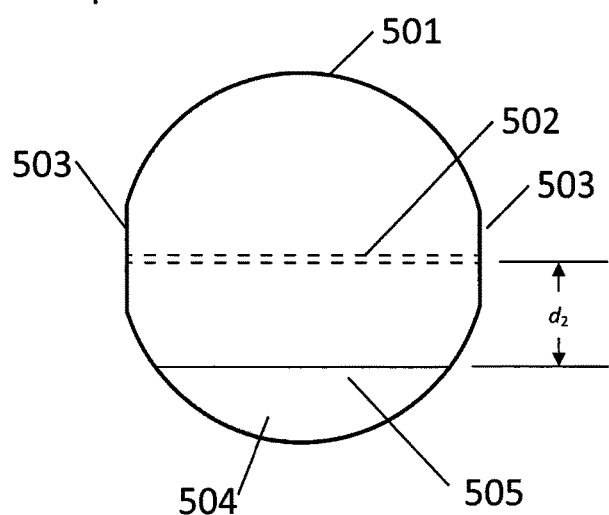
FIG. 5 shows top, side and front views of a flow cell compatible with an embodiment of the present invention displaying critical tolerance measurements.
Figure 5:
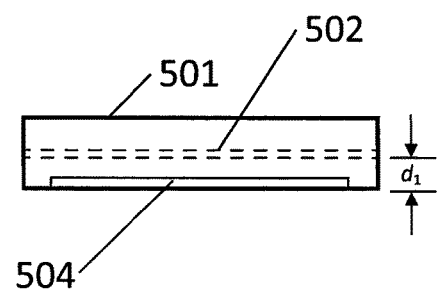
Figure 5:
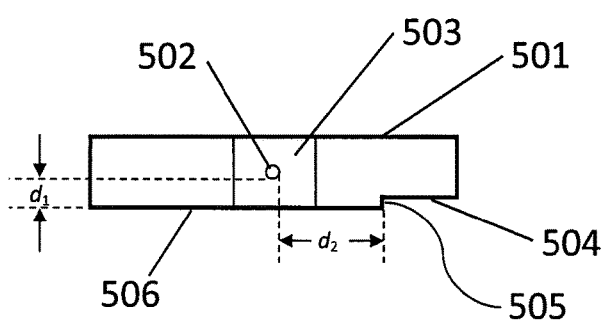

Let us now take a closer look at the flow cell utilized in this example embodiment of the invention. The reduction of stacked tolerances in the present invention and strict tolerance requirements for key elements of the flow cell manufacture permit independent glass cells to be interchanged with independent light scattering instruments. The cell 501 in FIG. 5 has a right cylindrical shape with the bore 502 machined through a radius of the cylinder. Two flat faces 503 are machined into the cell at the intersection of the bore 502 with the circumference of the cell 501. A flat step 504 is machined into one edge of the cell, generally parallel to the bore, however this preferred orientation should not be considered limiting. In this embodiment, the most critical measurements of manufacture are labeled $d_1$ and $d_2$ in FIG. 4. The vertical distance $d_1$ between the edge of the bore 501 on each of the flat faces 503 and the flat bottom of the cell is one such critical measurement. The second, $d_2$, is the horizontal measurement between the edge of the bore 502 and the inner edge 505 of the step 504. It is also critical that the bottom surface of the cell 506 be flat across the entire surface within strict tolerances. When these critical elements are fabricated within the strict tolerances required, problems traditionally associated with alignment of replacement cells will not be present with the inventive assembly presently disclosed.

Figure 6:
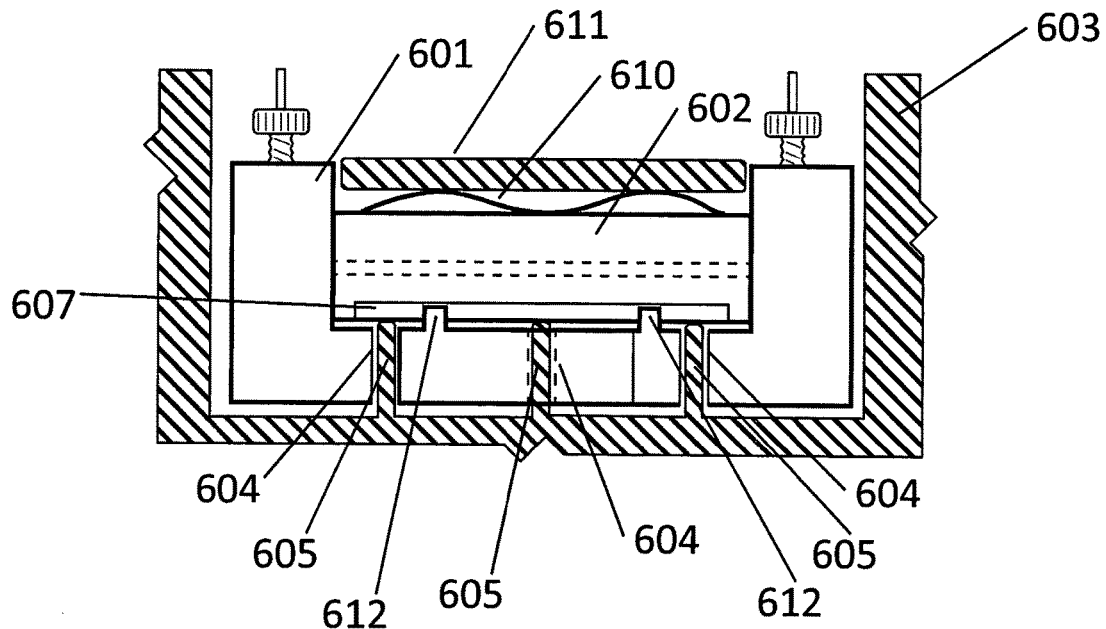
FIG. 6 shows side and top views of a floating flow cell manifold wherein alignment elements are in contact with the flow cell in several embodiments of the invention.
Figure 6:
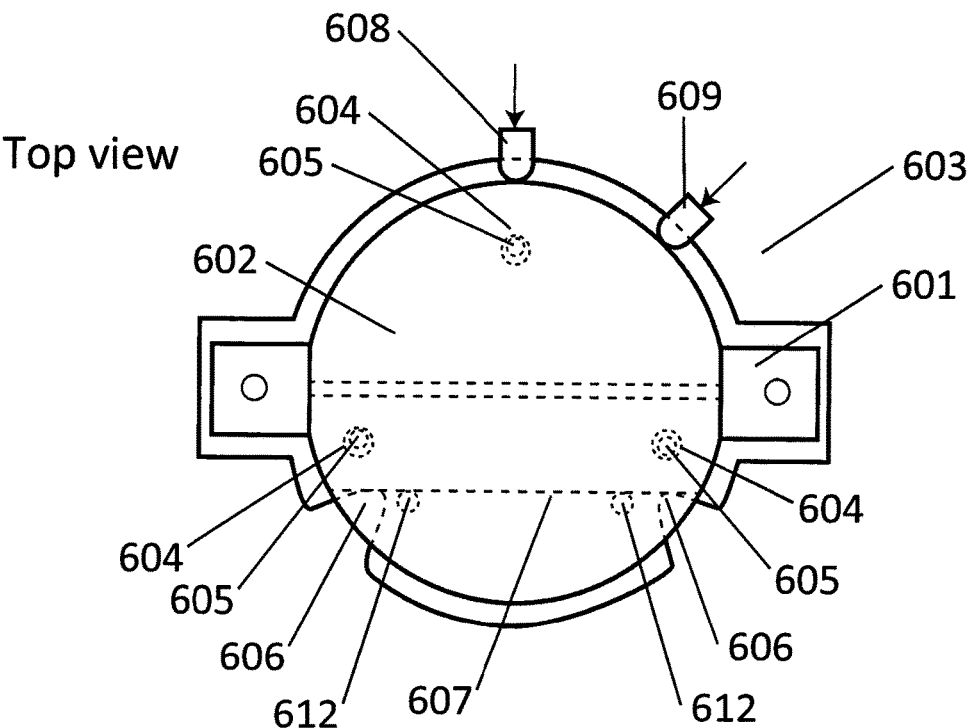

The next element of the inventive design is the read head which is designed to mechanically register directly to the flow cell rather than to the manifold as in previous MALS system designs. FIG. 6 shows some critical alignment elements of the cell/read head interface for an embodiment shown in FIG. 4. As mentioned above, the manifold assembly 601 holding the flow cell 602 floats within the read head 603 without necessarily making rigid contact thereto. The three holes 604 machined into the bottom of the manifold assembly allow vertical alignment posts 605 that are rigidly connected to the bottom of the read head to come into direct contact with the flow cell glass, defining the horizontal plane of the flow cell irrespective of any lose tolerances between the floating manifold and cell. As with the flow cell bottom plane defining contacts within the manifold, the vertical alignment posts of the read head may be either precision machined flat topped posts, generally cylindrical in body shape, though they may take other forms as well, or these posts may have hemispherical ends, such that a single point of contact for each of the three posts defines the plane upon which the cell sits within the read head. Bosses 606, which are generally rounded protuberances from the body of the read head, provide horizontal alignment by coming into contact with the precision machined vertical surface of the flow cell step 607. One ball plunger 608, generally integrated into the read head, applies a horizontal force to the cell, pushing the cell step against the rounded bosses 606 ensuring horizontal alignment of the cell bore to the read head mounted laser. Horizontal alignment is guaranteed by the strict tolerance $d_2$ discussed above. A second ball plunger 609 may be employed to provide additional pressure driving the cell step 607 against the alignment bosses 606 and additionally improve the stability of the seating of the floating manifold 601 within the read head 603. To improve clarity in FIG. 6 the horizontal planar alignment posts between the bottom surface of the cell and the manifold (elements 415 of FIG. 4) are not shown, however the pins 612 defining horizontal alignment (elements 417 of FIG. 4) between the manifold and the cell step 607 are shown to facilitate the visualization of the independent horizontal alignment of the cell 602 to the read head 603 as well as the cell 602 to the floating manifold 601. Once the manifold assembly is seated within the read head a compressible element 610, such as a wave washer, gasket or o-ring is sandwiched between the flow cell 602 and a top plate 611 which is connected directly to the read head 603 without coming into contact with the manifold assembly 601, thus maintaining the floating nature of the manifold while simultaneously applying a downward force, pushing the flow cell 602 onto the alignment posts 605 and defining, thereby the horizontal plane of the bottom of the cell. Thus vertical alignment of the cell is likewise guaranteed by the strict tolerance $d_1$ discussed above. Therefore, a laser mounted in the read head that is aligned to any appropriately fabricated flow cell adhering to the critical specification tolerances $d_1$ and $d_2$, will be properly aligned to any other flow cell contained in any other floating manifold which also adheres to the $d_1$ and $d_2$ specifications, and it is by this inventive means of decreasing the stacked tolerances and controlling a handful of strict specifications, that interchangeable flow cells between light scattering detectors is enabled. As was the case with the alignment elements between the cell and the manifold, exact-constraint design is employed by the three alignment posts 605 in contact with the planar bottom surface of the cell and the two alignment bosses 606 in contact with the step define the relative position of all elements of the manifold to all elements of the flow cell. This configuration of flow co-linear with the beam is sometimes referred to as a horizontal flow cell. In this embodiment the critical degrees of freedom that must be constrained are pitch, yaw, roll and translation perpendicular to the beam, however, the position of the cell parallel to the beam is not as critical to an effective light scattering measurement, as small deviations will vary only the position along the bore of the scattering volume, but not cause issues relating to the beam actually passing through the sample volume which would be the case if, for example, the position of the cell were shifted perpendicular to the beam, or out of the X-Y plane by the measurement of the bore diameter. Therefore we will consider that this embodiment requires five degrees of freedom to be constrained.

Figure 7:
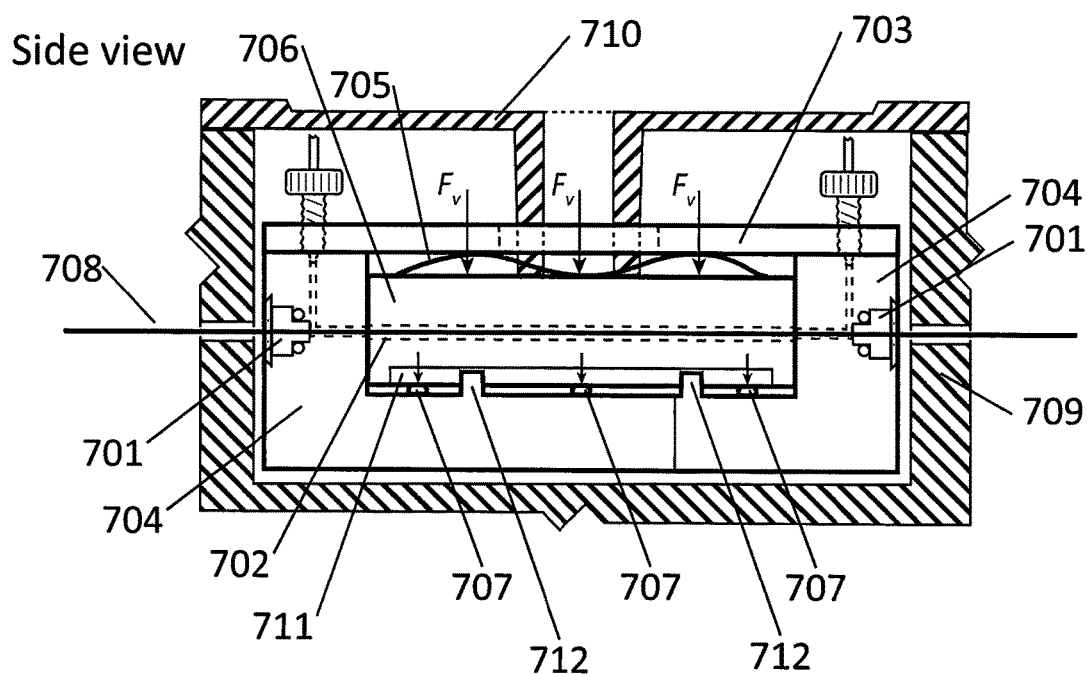
FIG. 7 highlights alignment elements between the manifold and the flow cell utilized in several embodiments of the invention by showing side and top views of various elements of an inventive assembly. Note the top view does not show read head elements.
Figure 7:
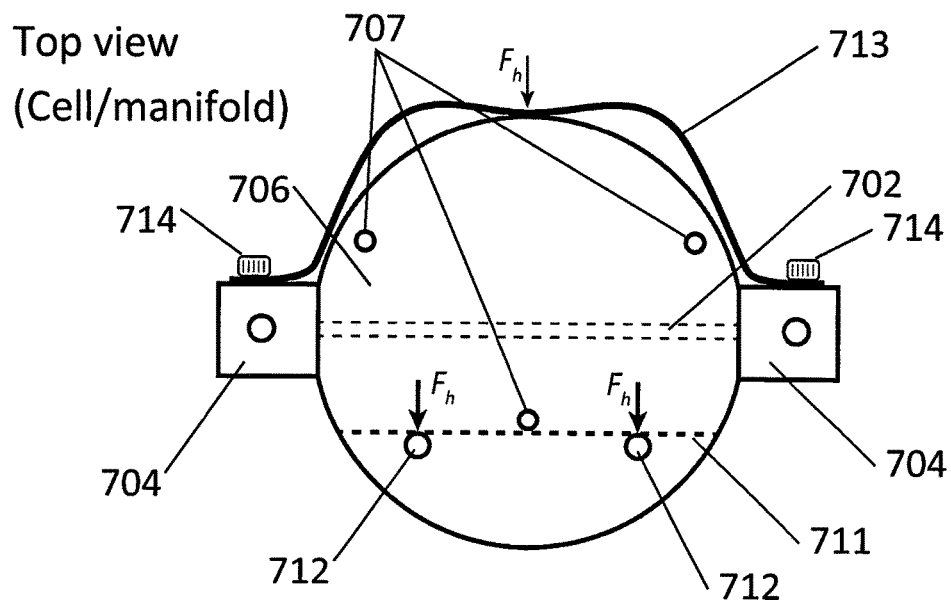

In order to further enhance the reproducibility and maintenance of alignment of interchangeable flow cells and cell assemblies disclosed thus far, a preferred embodiment of the invention shown in FIG. 7 employs means for applying a force between the manifold and the flow cell to maintain proper alignment between the windows 701 and the cell bore 702. In this embodiment a top manifold plate 703 is rigidly connected to the main manifold body elements 704. The top manifold plate 703 is generally connected to the manifold body elements 704 by means of threaded screws (not shown), but may also be connected by other means such as a clamping mechanism. A vertical force providing means 705, such as a wave washer, spring, gasket or o-ring, provides a downward force $F_v$ (indicated in FIG. 7 by arrows) on the flow cell 706, actively pushing it against the manifold alignment posts 707, which define the plane upon which the bottom of the flow cell 706 rests. As these force applying elements assure the bore 702 is in alignment with the windows 701, it guarantees that the beam 708 generating laser housed in the read head 709 will pass properly through both the windows 701 and the bore 702. It is important to note that the cell-to-read head vertical alignment posts 605 shown in FIG. 6 are still present in this embodiment, though they are not shown for the sake of clarity in FIG. 7. And as shown in FIG. 6, a read head top plate 710, though modified as shown in this figure, still enables the application of a downward force directly to the flow cell, driving the cell against the read head alignment posts (not shown). In the currently presented embodiment, the read head top plate itself acts as a spring element pushing downward on the flow cell without the need of a wave washer, o-ring or other extra force generating element. This is enabled by the read head top plate 710 having a slight concave curvature, and thus when rigidly connected to the top of the read head 709 it deforms slightly, with the resulting mechanical stress providing the downward pressure to the flow cell 706. The portion of the read head top plate in contact with the top of the flow cell 706 extends through a hole in manifold top plate 703. The top view presented in FIG. 7 does not show the elements of the read head in order to clearly show the critical elements of the presented embodiment. In order to provide a horizontal force $F_h$ driving the flow cell 706 and its incorporated horizontal alignment step 711 against the manifold horizontal alignment pins 712, a spring element 713 is connected by connection means such as threaded screws or bolts 714 screwed into each manifold element 704. This spring element, which may be a properly formed strip of sheet metal, or leaf spring, the deformation of which, when connected to the manifold and in contact with the flow cell provides the desired horizontal force. It should also be noted, that in this embodiment, the spring element 713 in contact with the flow cell 704 may also act as the contact point for one or more of the force generating ball plungers 508 and 509 that apply force to the flow cell to drive it against the read head rounded horizontal alignment bosses 506, the spring element 613 can therefore both apply the necessary cell/manifold horizontal alignment force as well as providing protection to the cell itself which might otherwise be scratched by the contact of the ball plunger 608 or ball plungers 608 and 609 if they were to make direct contact with the cell surface when the manifold/cell assembly is placed into the read head. It should also be noted that the spring element 713 need not be, and generally is not, the same height as the flow cell 704. In general the spring element extends only partially up the up the height of the cell, thus permitting optical access in a horizontal plane, to the flow cell bore 702, permitting, thereby, light scattering detectors to be placed at any number of angles about the bore on both sides of the cell. Alternately, the spring element may be a leaf spring with an opening along its horizontal axis, permitting optical access in a horizontal plane to the bore 702 while applying the desired horizontal force near the top and bottom of the height of the cell, thus providing a more uniform pressure. This embodiment not only promotes simple alignment of the elements during assembly, but mitigates misalignment during operation due to such causes as vibration or jarring of the instrument by actively pushing the elements back against their alignment fixtures.

It should be noted that the right cylindrical shape common to many light scattering detectors, such as the DAWN HELEOS (Wyatt Technology, Goleta Calif.), should not be considered a limitation of the present invention. For example, the lensed flow cell described by Trainoff in U.S. Pat. No. 982,875 (issued Jul. 19, 2011) could also be compatible with the present invention. In addition perpendicular flow cells discussed previously could also benefit from the present invention, extending the invention's utility to use with modern UHPLC systems. Further, while this disclosure is primarily concerned with MALS systems, use of the term MALS should not be considered limiting, as the invention disclosed herein is also compatible and beneficial to other flow through light scattering instruments including low angle light scattering (LALS) and right angle light scattering (RALS) instruments. In addition, dynamic light scattering (DLS) instruments also benefit from the present invention. DLS measurements can be taken independently or concurrently with MALS, LALS or RALS data. All light scattering instruments involving flow or stop-flow instruments are compatible with the present invention. Therefore throughout the specification the term MALS is generally used, as is the parallel flow cylindrical cell merely to simplify explanation, and thus should not be considered limiting at any point nor should any embodiment discussed herein as an exemplar be considered limiting.

Figure 8:
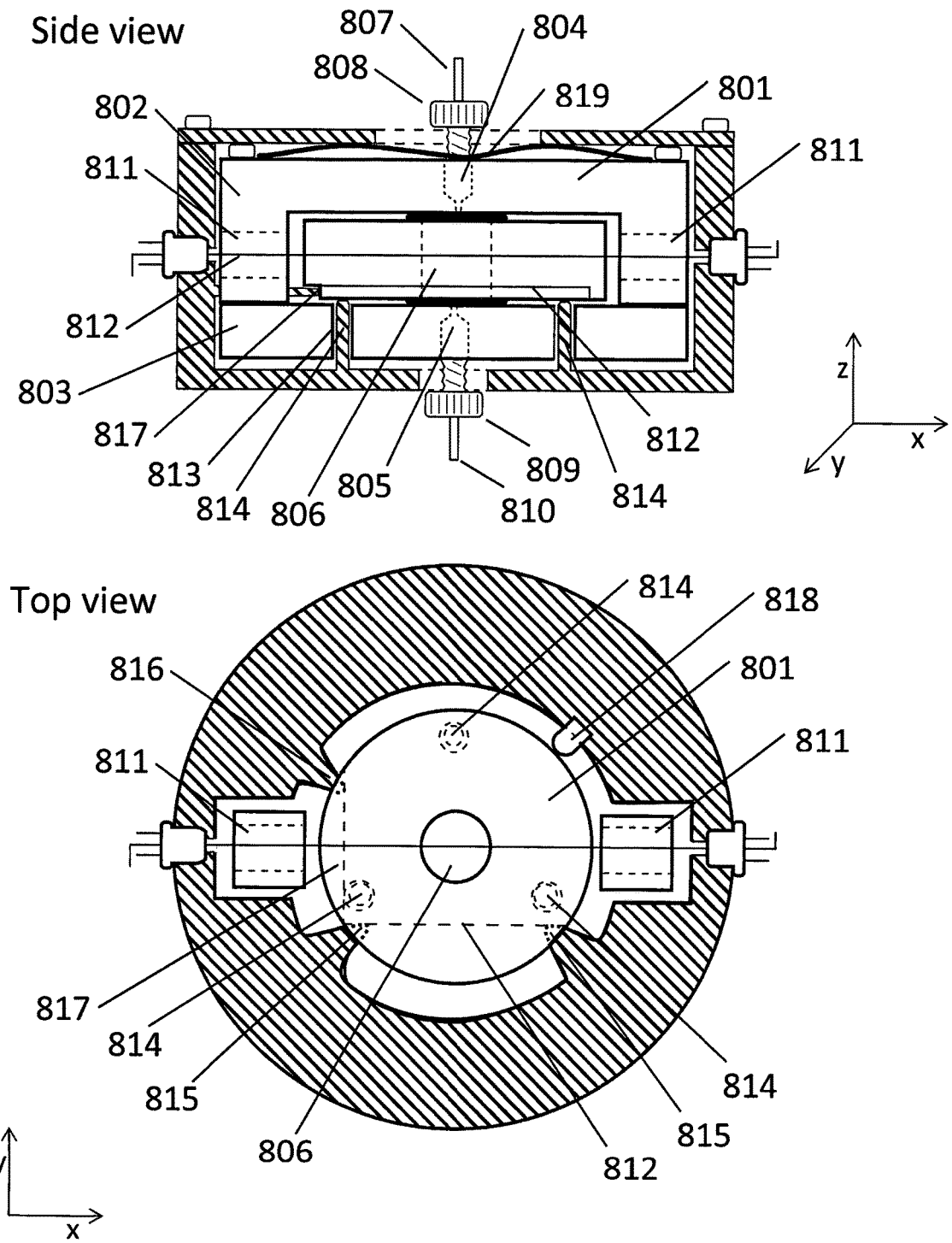
FIG. 8 shows side and top views of an inventive embodiment of a vertical flow cell held within a removable, floating manifold and mounted within a read head.

For another example of how exact-constraint design is used to simplify the mounting and alignment of the sample cell according to the present invention, consider the embodiment including a "vertical" flow cell according to the invention shown in FIG. 8. As discussed above, the vertical flow cell 801 is one wherein the flow is perpendicular to the direction of the beam 802, that is to say the beam crosses the sample laterally with respect to the direction of the sample flow. In this case there are fewer critical degrees of freedom in need of constraint associated with the positioning of the cell. With vertical flow through the cell and horizontal laser beam perpendicular to the flow, it is critical to constrain the position of the cell in the x-y plane. Pitch and yaw constraints are also important in order to properly align the detectors to the measurement volume near the center of the cell. However, roll, or rotation about the center of the cell, and position in the z direction are less critical, and therefore these degrees of freedom need not be constrained exactly by means of exact-constraint design for embodiments that use a vertical flow cell. There are various means by which the cell may be positioned within the read head, and, as the containing manifold need not house optical windows, the registration of the cell to the read head is made yet simpler. FIG. 8 shows an embodiment of the invention with a vertical flow cell 801 which utilizes a floating manifold similar to that described in above horizontal or co-linear flow embodiments. The flow cell 801, as before, is sandwiched between a top and bottom manifold 802 and 803. In this case the manifold serves primarily to provide inlet 804 and outlet 805 means to the measurement channel 806. A length of tube 807 is seated in the inlet port 804 with a fitting 808. Similarly the outlet tubing 809 is fitted into the outlet port 805 with a fitting 810. The manifold may house other elements such as inline filters, flow distributors, delay volumes, and sealing means, such as o-rings, etc., in its body, and/or within the flow path between the inlet and/or outlet tubing and the measurement channel 806. Holes 811 machined into the manifold 802 permit access of the laser beam 812 to the measurement channel 806. Alternately, the holes 811 may give optical access to the measurement channel to light scattering or other detectors, and the laser may be directed rather through the open side of the manifold, for example, perpendicular to the openings 811. It should be noted that in this configuration, the holes need not contain optical windows, and maybe significantly oversized, thereby obviating the need to carefully align laser or detector access there through. However, windows or other optical elements such as filters may be placed into these portals 811 as appropriate. The flow cell 801 may incorporate an alignment step 812. Further, either the top or bottom manifold 802, 803 has machined, there trough means, such as a hole or holes 813 by which alignment posts 814 extending from the read head may make contact with the planar bottom surface of the cell, defining thereby the x-y plane of the cell 801 relative to the read head. Alignment bosses 815 incorporated into the read head come into contact with the step, defining thereby the position of the measurement channel 806 along the y-axis relative to the laser beam. In most cases the position of the channel along the x-axis should also be constrained, particularly when the measurement channel has a circular cross section. In this case the alignment step 812 may be L shaped, and a third, alignment boss 816 will come into contact with the alignment step along the y-axis 817. When the all three alignment bosses are in contact with the step, the position of the measurement channel 806 will be exactly constrained in the x-y plane. Force may be applied from the read head to the cell from the side to drive the step onto the alignment bosses by means such as a ball plunger 818. And force may be applied opposite the alignment posts 814 within the read head 811 to the cell 801 or to the manifold 802, by means such as a wave washer 819, o-ring or gasket, to drive the cell 801 directly against the alignment posts 814. Thus, once again, the manifold floats, and it is the cell is directly registered to the read head. However, in this embodiment, it is not necessary that there be optical alignment between any elements within the manifold to the cell, thereby simplifying the step of combining the cell-manifold assembly.

Further simplifications are made to the system by more efficient utilization of exact constraint design, and permitting the manifold elements to float more completely or to be themselves incorporated into the read head. Consider the example embodiment shown in FIG. 9 where the outlet port 901 is an element of the read head itself, and the read head 902 is shaped so as to take advantage of the cylindrical nature of the sample cell 903. The V shaped end 904 the read head cavity comprises two vertical flat faces 905 and 906. When the cell 903 is placed into the cavity within the read head 902, the two lines of contact between the faces of the V channel 904 and the cylindrically shaped flow cell 903 constrain the cell 903 in all critical degrees of freedom. A horizontal force is applied to the cell by means such as one or more ball plungers 905 to firmly drive the outer cell wall against the V surfaces. The sample outlet 901 from the channel 906 is sealed with an o-ring 907 or gasket to with the outlet port 901 incorporated into the read head 902. The inlet into the measurement channel 906 is coupled with a sealing means 908, to an inlet port assembly 909; this assembly applies a downward pressure onto the cell, causing the o-rings 907 and 908 to seal. This pressure can be applied by any number of means such as a top flow assembly 909 comprising a flow port 910 to which inlet tubing 911 may be connected by means of a fitting 912, and which is screwed into a top plate 913 connected to the read head 902 itself by means such as screws 914, bolts or clamps. In this embodiment, the manifold is almost completely removed from the system. Within in the V section of the read head either the laser 915 or a photodetector may be placed. If the laser occupies this space, it may be beneficial to employ more than one force generating elements 905 on the opposite side of the cell in order to permit optical access to the beam 916 as it emerges from the far side of the cell. For example, by placing two ball plungers 905 each 45° from the beam path, equal pressure can easily be applied to drive the cell into the V channel. If the cell is of sufficient height, two ball plungers could also be used in line with the beam 916, but placed above and below its eventual intersection with the read head, thus applying uniform force directly into the V channel while still being out of the path of the laser and permitting the emerging beam to fall upon a laser monitor element 917. Additionally other means of applying horizontal pressure may be utilized, such as a leaf spring containing a hole to allow passage of the beam through the cell. While it may be simplest to include the laser 915 at the apex the V channel 904 of the read head 902, there may be many reasons to choose another configuration, such as the beam 916 traversing the measurement volume perpendicular to the direction of the V channel 904, or for that matter, it may be advantageous for the beam 916 to traverse the cell 903 at any other arbitrary angle in order to maximize both the uniformity of force driving the cell 903 against the V groove 904 while also maximizing the efficiency of the positioning of light scattering detectors 918 relative to the beam direction.

Figure 9:
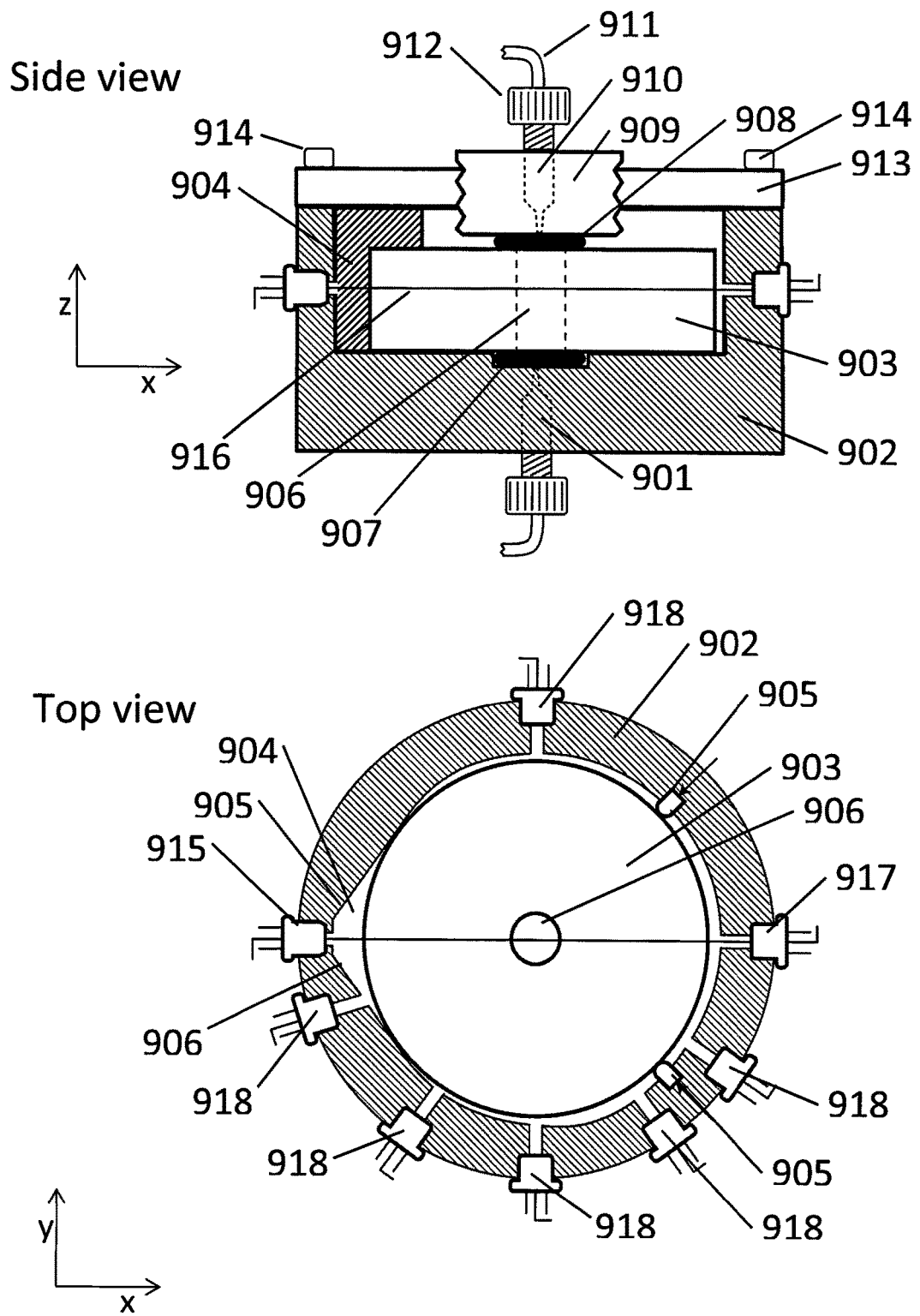
FIG. 9 shows side and top views of a vertical flow cell with critical translational and rotational degrees of freedom restrained as it sits directly within the read head without the need for a separate manifold element utilizing the method of exact-constraint design.
Figure 10:
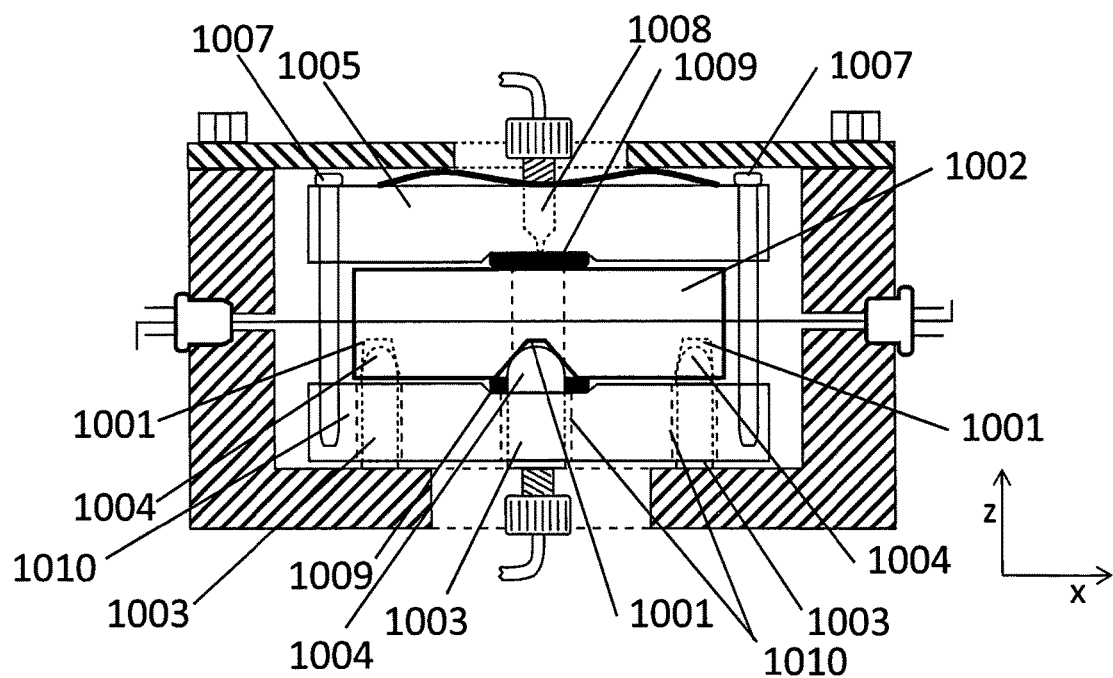
FIG. 10 exhibits a side view of a vertical flow cell held within a removable, floating manifold, and registered directly to the read head with critical degrees of freedom restrained utilizing the method of exact-constraint design. The bottom view shows only the flow cell and its registration elements.
Figure 10:
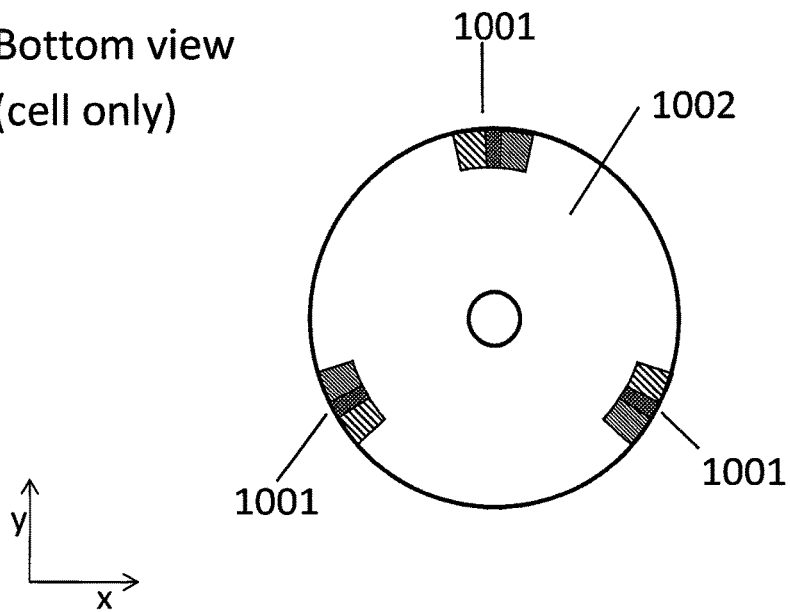

FIG. 10 illustrates elements of a similar embodiment also employing exact-constraint design. In this case the "three-V" constraint system is used. By incorporating three precision machined V grooves 1001 into the cell 1002 itself, and incorporating three precision positioned spheres or, perhaps more practically, posts 1003 with hemispherical tops 1004, the cell 1002 can have all critical degrees of freedom constrained with no further alignment necessary. This embodiment can be utilized either with the outlet port incorporated directly into the read head itself (as in the example shown in FIG. 9), or the inlet and outlet flow to the cell 1002 can be restricted with a floating manifold unit as shown in FIG. 9. In this example the manifold comprises top 1005 and bottom 1006 portions connected by bolts 1007, and each manifold element comprises a port element 1008, with sealing means 1009 located between each element and the cell itself 1002. Additionally, the floating manifold must allow access to the three hemisphere topped posts 1003 to the V grooves 1001 incorporated into the cell 1002 by means such as one or more holes 1010 contained within the bottom manifold element 1006. The port elements 1008 may also hold additional elements such as inline filters, flow distributors, and/or dead volumes. It should be noted that the floating manifold presented may also replace the read head incorporated outlet port in other embodiments, in particular that shown in FIG. 9. Again, as the positioning in the z-axis is not critical some loosening of the tolerances in any vertical positioning elements is permitted without loss of signal quality. It should be noted that the incorporation of additional geometries into light scattering cells, such as the V grooves machined into their surface in the embodiment presented in FIG. 10, may give rise to unwanted reflections and stray light issues under certain circumstances, and for that reason it is often desirable to make the scattering cells of the simplest geometry possible, such as the traditional cylinder with a bore drilled through a diameter. If reflections and stray light are of particular concern, this embodiment can employ a section of black, or appropriate wavelength absorbing, glass adhered or contact bonded to the main body of the cell, where this region of black glass is the area containing the V grooves, or other necessary exact constraint design geometries, hence decreasing the likelihood that these added geometries will cause optical problems.

In order to investigate the efficacy of the inventive apparatus with regard to the interchangeability of flow cells and/or manifolds for a given light scattering detector, experiments were performed using a retrofitted DAWN® HELEOS® II light scattering photometer (Wyatt Technology Corporation, Goleta, Calif.). These experiments further helped to define the tolerances on the key specifications which must be met in order for the system to perform properly. The flow cells used in these experiments were fabricated from fused silica and had dimensions of approximately 30 mm in diameter, 11 mm in height with a bore diameter of 1.2 mm in the same general configuration as the cell shown in FIG. 4. A control cell was mounted in the floating manifold and placed in the retrofitted read head of the light scattering instrument. The laser was then aligned to the control cell such that it passed through the center of the bore of the flow cell. The laser was a 658 nm diode laser with corrective optics designed to minimize the beam width common in MALS detectors.

Figure 11:
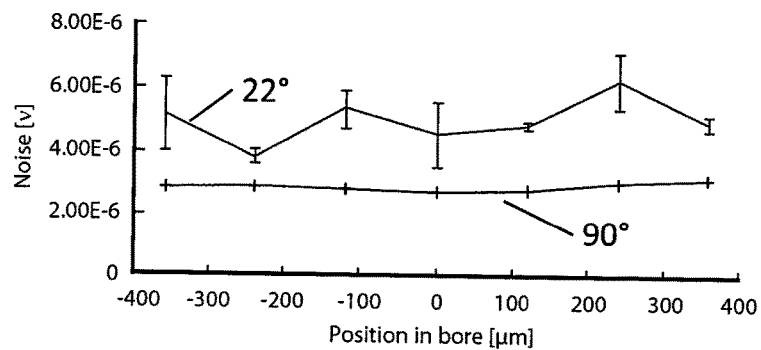
FIG. 11 shows noise and baseline levels on the 22° and 90° detectors as the laser was swept vertically and horizontally parallel to the direction of the bore of a fused silica flow cell with a bore diameter of 1.2 mm.
Figure 11:
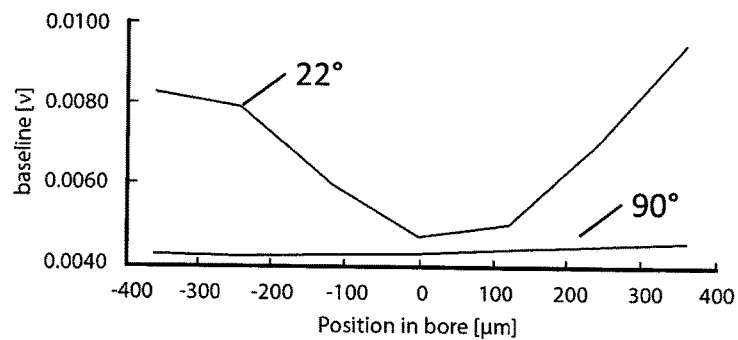
Figure 11:
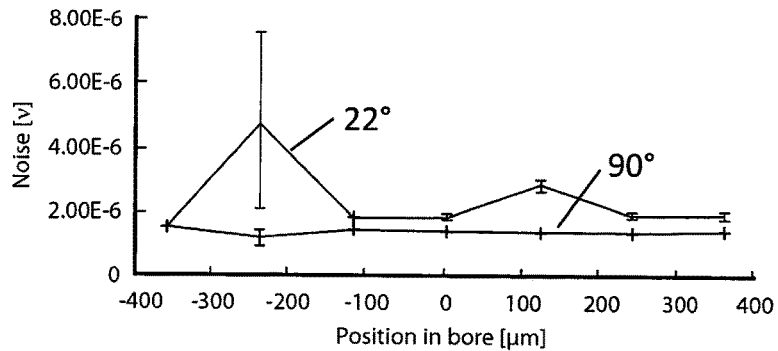
Figure 11:
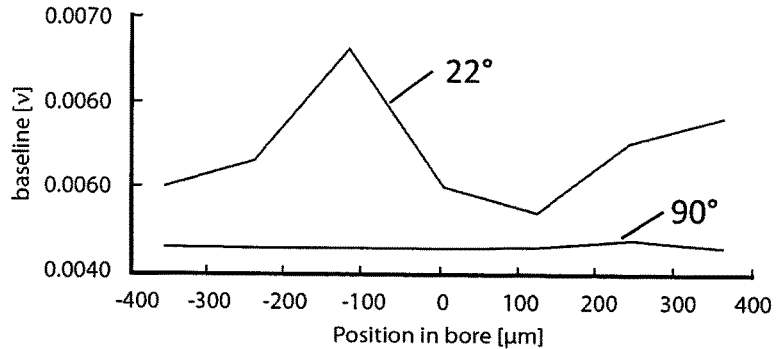

Once properly aligned the laser was swept horizontally and vertically while the 90° and 22° light scattering detector signals were monitored. This test determined a bore diameter safe region by measuring the laser position offset from the center of the bore that yielded results at acceptable baseline and noise levels. Holding the laser fixed in one direction and sweeping it both vertically and horizontally from 350 µm from the center of the bore to −350 µm had no appreciable effect on noise levels and only affected baseline levels in the low angle detector as shown in FIG. 11.

Figure 12:
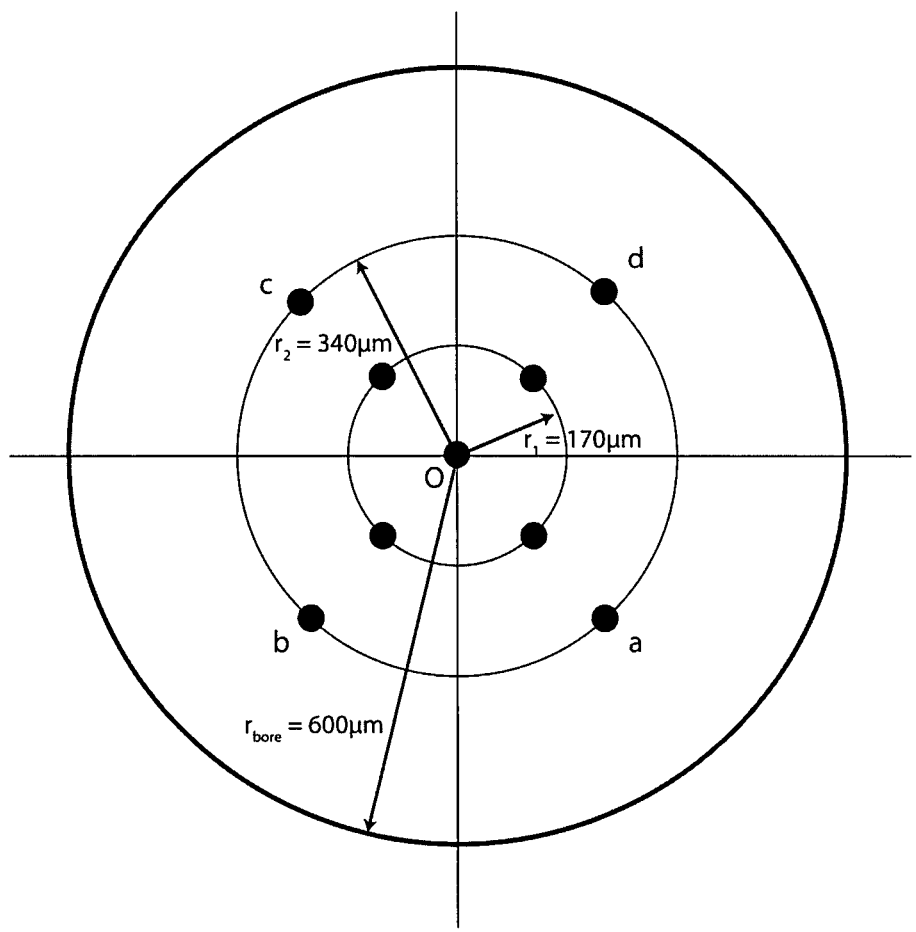
FIG. 12 shows the beam position at a cross section of the bore for BSA experiments used to determine a safe region beam for position variation which produce acceptable results.

The next experiment was to perform standard aqueous chromatography injections of bovine serum albumin (BSA)

with the laser located at positions offset from the center of the bore at radii of 340 µm and a more restrictive 170 µm. The positions of the laser in a cross section of the bore are shown in FIG. 12. The resulting weight averaged molar masses were calculated for each run are displayed in Table 1. The acceptable range for BSA molar mass is 63.08 kDa-69.72 kDa. Therefore, as the results of Table 1 show, only at two positions did the measurements fall outside the specification range.

TABLE 1

BSA weight averaged molar mass measurements with laser at different distances and positions from the cross-sectional center of the cell bore

| Position | BSA Measured Molar Mass (kDa) | |
|---|---|---|
| | $r_1$ (170 µm) | $r_2$ (340 µm) |
| A | 63.52 | 62.66 |
| B | 67.10 | 68.59 |
| C | 66.55 | 67.31 |
| D | 64.52 | 62.57 |

The results shown in the above experiment defined a probable safe region within 170 µm radius about the center of the bore cross section. These results were confirmed by fractionating 200 kDa and 30 kDa polystyrene particle suspensions with a chromatography system using toluene as the mobile phase. The acceptable molar mass range for 200 kDa polystyrene is 190-210 kDa, and 25-35 kDa for the 30 kDa polystyrene. The results of these runs are shown in Table 2. Not only did every run fall well within the specification, the results were very consistent, thus confirming the safe region of at least 170 µm radius about the cross sectional center of the bore.

TABLE 2

Polystyrene latex injections into a size exclusion chromatography system with toluene as a mobile phase.

| Position | Measured Molar Masses (kDa) – r = 170 µm | |
|---|---|---|
| | 200 kDa | 30 kDa |
| O | 205.3 | 29.36 |
| A | 204.6 | 29.22 |
| B | 203.8 | 29.27 |
| C | 204.4 | 29.22 |
| D | 204.6 | 29.31 |

Figure 13:
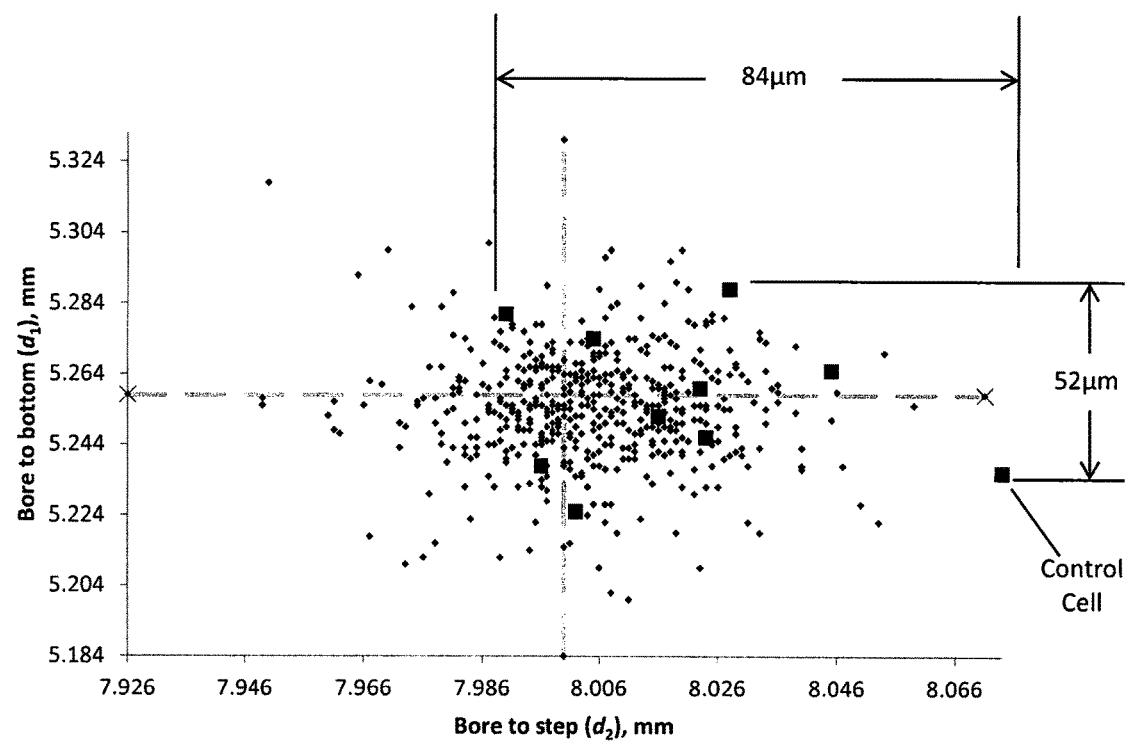
FIG. 13 shows the variation of two critical alignment measurements on a flow cell according to one embodiment of the invention.

The results of the above tests indicating a safe region of 170 µm radius inside the bore suggested that aligning to the read head with this inventive design provides adequate accuracy in bore position to be able to interchange flow cells without re-aligning the laser. The deliverable specification for bore position tolerance is +/−75 µm with respect to the alignment features previously discussed as measurements $d_1$ and $d_2$, thus even maximum deviation within the specification still falls well within the safe region. The measured distances of $d_1$ and $d_2$ for a series of ten test cells and recorded historical measurements of cells are presented in FIG. 13. Historical data is denoted by the small diamonds whereas the larger squares indicate test cells. As noted in FIG. 13, the largest deviation between test cells in $d_2$ is 84 µm, and the largest deviation in $d_1$ is 52 µm, well within the safe region discussed above. In order to practically confirm the efficacy of the invention, the control cell discussed above was replaced within the read head of the retrofitted MALS instrument with each of the test cells indicated as square markers in FIG. 13. After interchanging cells, with no alignment procedure performed, BSA and polystyrene injections were made, as before. As is evident from the data presented in Table 3, all of the cells provided data well within the acceptable values, thus confirming the ability of interchange flow cells with the inventive system described herein.

TABLE 3

Chromatography results for ten test cells replaced within a retrofitted read head and utilizing a floating manifold head without performing realignment procedures..

| | 1 (control) | 2 | 3 | 4 | 5 | 6 | 7 | 8 | 9 | 10 |
|---|---|---|---|---|---|---|---|---|---|---|
| 200 k PS MM | 202.3 | 203.8 | 203.7 | 203.5 | 203.9 | 203.3 | 203.5 | 203.4 | 203.6 | 202.4 |
| 30 k PS MM | 29.11 | 29.12 | 29.2 | 29.1 | 29.15 | 29.12 | 29.18 | 29.14 | 29.06 | 29.12 |
| BSA MM | 63.83 | 64.71 | 63.5 | 65.36 | 65.35 | 65.13 | 64.2 | 65.12 | 66.18 | 65.86 |

While the benefits of the present invention are useful to light scattering detectors in general, they are of particular relevance in the field of Process Analytic Technology (PAT) where ongoing reactions are monitored for significant changes to indicate when a particular reaction is complete, or the product being produced has reached the limits of its acceptable range. For example, in the polymer industry PAT is used to monitor reactions which produce polymers from monomeric species. See, for example, U.S. Pat. No. 9,568, 462 B2, "Methods and instrumentation for during-synthesis monitoring of polymer functional evolution," by W. F. Reed (Issued Feb. 14, 2017). As Reed explains, in continuous reaction processes, where one product composition is changing to another, it is essential to be able to monitor the online state of the product and determine the point of acceptable changeover of one product composition to another. Reed describes monitoring molar mass values in order to determine the amount of the fundamental residual monomer still present in the reaction stream while producing the desired polymer.

Another example of an industrial process that can benefit from PAT includes the purification of a given product. This process involves purification steps wherein a product containing contaminants is passed through a system intended to permit passage of the product but retain the majority of contaminants. For such systems the purification mechanism often has a limit to the quantity of contaminants which may be retained. Once this practical threshold is reached, contaminants may begin to "break through" the purification device and become part of the product stream. One example of this type of process frequently used in the pharmaceutical industry is flow-through process chromatography, and variations include flow through hydrophobic interaction chromatography and flow through ion exchange chromatography. For these cases protein monomer, dimer, and higher order oligomers are all contained within an unpurified material. Only one of these species is desired in the final product, e.g. the protein monomer. The chromatographic system is tuned such that the desired species, e.g. monomer, passes through the chromatographic system, and the undesirable species, e.g. dimers and higher oligomers, adhere to surfaces within the chromatographic system. When material first begins to flow through the system, there is a large surface area available to which contaminants can adhere. Eventually, the adhesion sites become filled, and more and more undesirable species pass through the chromatographic system. This product stream elution maybe monitored by a system, such as one comprising light scattering and concentrations detectors. This detection system can determine the real-time value of the molar mass, which increases as more of the eluent contains oligomers rather than almost exclusively monomer species. An increase in the monitored value of the molar mass beyond a pre-set given threshold marks the end of the purification run. Another PAT method involves affinity chromatography, also known as bind and elute chromatography. In this case, the desired sample is passed through a highly selective column specifically chosen such that the desired molecule interacts with the stationary phase and is thus bound within the column and is thus separated from the stream. Thus the contaminants, rather than being retained, are flushed first and the desired molecules are retained until a change is made to the solvent flow which releases the retained, purified sample. Similarly to, flow-through process chromatography, the molar mass of the eluting fractions can be monitored for changes which indicate the end of the purification process and trigger the change in mobile phase required to release the retained, purified sample from the column, which is then collected.

Utilizing the present invention in a PAT system offers the advantage of being able to not only replace the flow cell quickly, but, more importantly, to permit the replacement of key elements of the system reliably without the need to replace an entire instrument within the process environment. With the embodiments of the present invention used within a PAT system, the flow cell can be reliably removed and replaced without the need to requalify a new instrument in the process stream, and thus, for the first time, a process engineer without extensive experience with optical instrumentation, can, with little downtime, perform simple, turnkey maintenance to a PAT-MALS system. Whereas previously a dirty or permanently fouled cell might require an optical expert and/or extensive training to clean, and a permanently fouled cell may require the replacement of a complete instrument, and in all cases replacing the cell would require extensive re-evaluation and re-qualification within the PAT system, the present invention makes MALS instruments practical within a PAT environment.

Further, while traditional chromatography systems generally utilize extremely dilute solutions for measurement of properties of the liquid samples separated therewith, some PAT environments involve a much wider range of sample concentration. Some embodiments of the present invention enable the use of a light scattering detectors with very little preparative work and a much wider variation in sample composition than is true with traditional chromatography measurements. As discussed above, the critical alignment measurements $d_1$ and $d_2$ when combined with knowledge of the cross sectional radius of the sample bore define a "safe region" where variation in the position of the beam still produces quality results. Therefore, in PAT systems, one may increase the radius of the cross section of the bore two, three, four or more times while still mitigating beam steering due to changes in sample composition throughout the reaction process. Because of the decreased tolerance stacking in the present invention, utilizing these wide bore sample cells is possible in PAT systems.

As will be evident to those skilled in the arts light scattering and macromolecular characterization, there are many obvious variations of the methods and devices of our invention that do not depart from the fundamental elements that we have listed for their practice; all such variations are but obvious implementations of the invention described hereinbefore and are included by reference to our claims, which follow.

The invention claimed is:

1. An optical flow cell assembly comprising:
   a transparent flow cell;
   a manifold configured to contain the flow cell;
   a read head comprising
      a beam generating light source aligned to emit a beam of light along an axis of the read head; and
   wherein the read head is configured to be directly registered to the flow cell, thereby aligning the flow cell to the read head,
      wherein the read head further comprises
         a plurality of read head vertical alignment posts configured to contact at least one planar alignment surface of the flow cell to define a vertical read head-to-flow cell alignment plane perpendicular to the axis,
         a read head top plate configured to drive the at least one planar alignment surface against the read head vertical alignment posts,
         at least one read head horizontal alignment boss configured to contact an alignment step of the flow cell to define a horizontal read head-to-flow cell alignment plane perpendicular to the vertical read head-to-flow cell alignment plane, and
         a ball plunger configured to drive the alignment step into contact with the at least one read head horizontal alignment boss,
      wherein the plurality of read head vertical alignment posts is distinct from the read head top plate, is distinct from the at least one read head horizontal alignment boss, and is distinct from the ball plunger,
      wherein the read head top plate is distinct from the at least one read head horizontal alignment boss and is distinct from the ball plunger, and
      wherein the at least one read head horizontal alignment boss is distinct from the ball plunger.

2. The optical flow cell assembly of claim 1 wherein the manifold comprises:
   a liquid sample inlet port;
   a liquid sample outlet port;
   an inlet path coupled to an outlet of the inlet port;
   an outlet path coupled to the inlet of the outlet port; and
   wherein the inlet path and the outlet path are configured to direct a flow of a liquid sample from the inlet port through the flow cell and out of the outlet port.

3. The optical flow cell assembly of claim 2 wherein the manifold further comprises transparent optical windows configured to allow the beam to pass into and out of the flow cell.

4. The optical flow cell assembly of claim 2 wherein the manifold further comprises a plurality of post elements incorporated into a surface of the manifold,
wherein the plurality of post elements is configured to contact the flow cell to determine a vertical registration of the flow cell relative to the manifold.

5. The optical flow cell assembly of claim 4
wherein the plurality of post elements comprises three post elements configured to define a plane upon which the flow cell rests,
wherein the at least one planar alignment surface is configured to sit upon the plane upon which the flow cell rests.

6. The optical flow cell assembly of claim 5 wherein the manifold further comprises at least one manifold horizontal alignment element configured to contact the alignment step to determine a horizontal position of the flow cell relative to the manifold.

7. The optical flow cell assembly of claim 6
wherein a horizontal distance from a flow path through the flow cell to the alignment step defines a first critical tolerance, and
wherein a vertical distance from a bore through the flow cell to the at least one planar alignment surface defines a second critical tolerance.

8. The optical flow cell assembly of claim 7 wherein the manifold further comprises vertical holes configured to allow access to the at least one planar alignment surface.

9. The optical flow cell assembly of claim 8 further comprising a compressible element configured to generate a vertical force between the manifold and the flow cell to drive the at least one planar alignment surface against the plurality of post elements.

10. The optical flow cell assembly of claim 9 wherein the compressible element comprises a wave washer configured to be placed between the flow cell and a manifold top plate configured to be rigidly connected to the manifold.

11. The optical flow cell assembly of claim 10 further comprising a spring element configured to generate a horizontal force between the manifold and the flow cell to drive the alignment step against the at least one manifold horizontal alignment element.

12. The optical flow cell assembly of claim 11 wherein the spring element comprises a leaf spring configured to be rigidly connected to the manifold and configured to be in contact with the flow cell.

13. The optical flow cell assembly of claim 12 wherein the leaf spring defines an opening along a horizontal axis of the leaf spring,
wherein the opening is configured to permit access to the flow cell.

14. The optical flow cell assembly of claim 8 further comprising a spring element configured to generate a horizontal force between the manifold and the flow cell to drive the alignment step against the at least one manifold horizontal alignment element.

15. The optical flow cell assembly of claim 4 further comprising a compressible element configured to generate a vertical force between the flow cell and the read head to drive the at least one planar alignment surface against the plurality of post elements.

16. A method comprising:
containing an optical flow cell within a manifold such that the optical flow cell is aligned to the manifold; and
registering directly the flow cell to a read head with read head-to-flow cell alignment elements, thereby aligning the flow cell to the read head,
wherein the read head comprises a beam generating light source aligned to emit a beam of light along an axis of the read head
wherein the read head further comprises
a plurality of read head vertical alignment posts configured to contact at least one planar alignment surface of the flow cell to define a vertical read head-to-flow cell alignment plane perpendicular to the axis,
a read head top plate configured to drive the at least one planar alignment surface against the read head vertical alignment posts,
at least one read head horizontal alignment boss configured to contact an alignment step of the flow cell to define a horizontal read head-to-flow cell alignment plane perpendicular to the vertical read head-to-flow cell alignment plane and
a ball plunger configured to drive the alignment step into contact with the at least one read head horizontal alignment boss,
wherein the plurality of read head vertical alignment posts is distinct from the read head top plate, is distinct from the at least one read head horizontal alignment boss, and is distinct from the ball plunger,
wherein the read head top plate is distinct from the at least one read head horizontal alignment boss and is distinct from the ball plunger, and
wherein the at least one read head horizontal alignment boss is distinct from the ball plunger.

17. The method of claim 16 further comprising
providing a vertical force between the manifold and the flow cell,
thereby allowing the vertical force to drive a vertical alignment surface of the flow cell against a plurality of vertical alignment elements incorporated into the manifold,
thereby allowing, in response to the vertical alignment surface being in contact with the plurality of vertical alignment elements, the flow cell to be in proper vertical alignment with optical windows of the manifold.

18. The method of claim 17 further comprising
providing a horizontal force between the manifold and the flow cell,
thereby allowing the horizontal force to drive a horizontal alignment surface incorporated into the flow cell against a plurality of horizontal alignment elements incorporated into the manifold,
thereby allowing, in response to the flow cell being in contact with the plurality of horizontal alignment elements, the flow cell to be in proper horizontal alignment with the windows.

* * * * *